United States Patent

Stroh et al.

[11] Patent Number: 6,020,003
[45] Date of Patent: Feb. 1, 2000

[54] METHOD OF MAKING SPRAY-DRIED POWDERS WITH HIGH EDIBLE-OIL LOADINGS BASED ON NON-HYDROLYZED GELATIN

[75] Inventors: Friedemann Stroh, Southgate; David Bower, Trenton; Frederick Chaundy, Gross Ile; Jeffrey Finnan, Dearborn; Thomas Soblesky, Canton, all of Mich.

[73] Assignee: BASF Corporation, Mount Olive, N.J.

[21] Appl. No.: 09/027,597

[22] Filed: Feb. 23, 1998

[51] Int. Cl.⁷ .................................................. A61K 9/14
[52] U.S. Cl. ............................................. 424/489; 424/464
[58] Field of Search .................... 424/489, 464, 424/499, 439

[56] References Cited

U.S. PATENT DOCUMENTS

| | | |
|---|---|---|
| 3,564,097 | 2/1971 | Magid . |
| 3,608,083 | 9/1971 | Bunnell et al. . |
| 3,646,192 | 2/1972 | Magid . |
| 3,914,430 | 10/1975 | Cannalonga et al. . |
| 3,932,634 | 1/1976 | Kardys . |
| 3,947,596 | 3/1976 | Cannalonga et al. . |
| 3,959,472 | 5/1976 | Cannalonga et al. . |
| 3,962,384 | 6/1976 | Cannalonga et al. . |
| 4,711,894 | 12/1987 | Wenzel et al. . |
| 4,849,225 | 7/1989 | Mitsuhashi et al. ............ 424/439 |
| 4,870,196 | 9/1989 | Thorengaard . |
| 4,892,889 | 1/1990 | Kirk et al. . |
| 5,120,761 | 6/1992 | Finnan ............................. 424/499 |
| 5,478,569 | 12/1995 | Berneis et al. . |

*Primary Examiner*—Thurman K. Page
*Assistant Examiner*—William E. Benston, Jr.
*Attorney, Agent, or Firm*—Barbara V. Maurer; Joanne P. Will

[57] ABSTRACT

The present invention relates to a method for making spray-dried tablettable powders with high edible oil loadings based on non-hydrolyzed gelatin. Said edible oils can be vitamin, flavor and fragrance oils.

7 Claims, No Drawings

METHOD OF MAKING SPRAY-DRIED POWDERS WITH HIGH EDIBLE-OIL LOADINGS BASED ON NON-HYDROLYZED GELATIN

FIELD OF THE INVENTION

The present invention relates to a method of making spray-dried tablettable powders with high edible-oil loadings based on non-hydrolyzed gelatin. Said edible oils can be vitamin, flavor or fragrance oils and mixtures thereof.

BACKGROUND OF THE INVENTION

High potency vitamins, particularly the antioxidant ones, are regularly consumed as the health benefits of these vitamins are increasingly acknowledged in the scientific and lay press. However, as the high potency tablets grow larger and larger they approach the limits of swallowability. One way to limit the growth in the size of the tablets is to put more active vitamins with less carriers. To make the oil-soluble vitamins, such as vitamin E, suitable for tabletting they must be combined with some kind of carrier to form a tablettable powder where the oil does not interfere with tabletting. Additionally, the carrier must act as binder with other ingredients within the tablet. Up until now the limit of the content of vitamin E in such carriers has been around 75% (750 international units (IU)/g). However, high edible oil (e.g. vitamin E) loading results in tablets with poor characteristics such as low hardness, incomplete disintegration, oil spots on the tablets, oil inhibition of dissolution of trace components in the tablets. The art has attempted to solve the problems with high oil loading tablettable powders.

Specifically, U.S. Pat. No. 3,564,097 (Hoffman-La Roche) discloses multivitamin tablets containing high potency vitamin E (35 to 65% by weight) and an inert carrier such as hydrolyzed gelatin. Tricalcium phosphate is used as an excipient to enhance stability against cracking and oil bleeding.

U.S. Pat. No. 3,608,083 (Hoffman-La Roche) discloses high potency vitamin E powders having 40 to 60% by weight vitamin E and hydrolyzed gelatin. The high potency vitamin E powder is prepared by emulsifying the vitamin E and the hydrolyzed gelatin and then spray drying the emulsion.

U.S. Pat. No. 3,646,192 (Hoffman-La Roche) discloses multivitamin tablets containing high potency vitamin E (35 to 65% by weight) and an inert carrier such as hydrolyzed gelatin. Silica is used as an excipient to enhance stability against cracking and oil bleeding.

U.S. Pat. No. 3,947,596, U.S. Pat. No. 3,959,472, U.S. Pat. No. 3,914,430 and U.S. Pat. No. 3,962,384 (all assigned to Hoffman-La Roche) disclose spray drying processes for preparing a tablettable fat-soluble vitamin powder. The fat-soluble vitamin is about 60% by weight of the powder. Said powder is prepared by blending the fat-soluble vitamin with hydrolyzed gelatin in a sonic homogeneizer (e.g. Homo-Mixer®) to achieve an emulsion having a particle size of 1 to 3 microns. Said emulsion is then spray dried. Further, glidants (silicates) must be introduced into the spray chamber to prevent adhesion of the emulsion particles to the walls of the dryer.

U.S. Pat. No. 3,932,634 discloses an oil soluble vitamin solution comprising 10 to 55% oil soluble vitamins and dispersing agents such as polyoxyethylene sorbitan monooleate and polyethylene glycol 400 monooleate.

U.S. Pat. No. 4,711,894 (assigned to Henkel) discloses a dry free-flowing vitamin E powder comprising 20 to 60% vitamin E and 40 to 80% carrier selected from gelatin (preferably hydrolyzed) silica, starches or gums and a stabilizer selected from hydroxy or amino acids. Said vitamin powder is prepared by spray drying.

U.S. Pat. No. 4,870,196 discloses a method of preparing a free-flowing vitamin E powder by melting the vitamin E and wax and emulsifiers and powdering agents and spraying this mixture to form droplets.

U.S. Pat. No. 4,892,889 (assigned to BASF) discloses a process for making compressible (tablettable) vitamin powders. Said vitamin powder comprises 20 to 60% vitamin E and 6 to 46% non-hydrolyzed gelatin. An effective amount of a carbohydrate such as lactose or corn syrup or mannitol is added to the vitamin/gelatin emulsion, to aid in creating a stable emulsion. Said emulsion is suitable for spray drying to prepare the vitamin powder. Silicon dioxide is injected into the spray drying chamber to improve flowability of the powder.

U.S. Pat. No. 5,120,761 (assigned to BASF) discloses a free flowing spray dried vitamin E powder comprising 50% vitamin E and partially hydrolyzed gelatin.

U.S. Pat. No. 5,478,569 (assigned to Hoffman-La Roche) discloses powdered fat-soluble vitamin compositions comprising approximately 55% vitamin E and fish gelatin. The powder is prepared by spray drying an emulsion of the vitamin and the gelatin. The particle size of the emulsion is about $0.3\,\mu$ to $0.6\,\mu$.

Vitamin E for tabletting is generally sold in a powder form. The commercial standard is 500 iu/gram. Vitamin E is 1000 iu/gram in pure form. Therefore, a 500 iu/gram powder consists of 50% vitamin E oil. Recently, however, a powder which comprises 75% vitamin E and carriers such as fish gelatin, calcium silicate and silicon dioxide, is currently sold by Hoffmann-La Roche, Inc. This product has just been made recently available.

Surprisingly, Applicants have improved on the art of high oil loading tablettable powders. Specifically, Applicant's high oil loading tablettable powders are less greasy than currently available products; have better tabletting properties; and the oil loading can be as high as 90% to deliver more active ingredient in a smaller tablet.

Also, there are processing advantages to the present invention. At higher loadings of the active ingredient, less carrier is required which leads to cost savings. Since there is less carrier, less water is necessary to dissolve the carrier. Therefore, less energy is necessary to dry the powder and greater throughput is achieved. Because hydrolyzed or partially hydrolyzed gelatin is no longer needed, the extra processing cost and the need to control that processing step is obviated. Finally, the preparation of the present invention can be carried out in a "conventional" spray-dryer, i.e. cool air zone modified spray drying is not necessary because atomized droplet formation is not a problem. Thus, costly equipment modification is also obviated.

DEFINITIONS AND USAGES OF TERMS

Gelatin Characterization

Gelatin is most typically characterized by its "Bloom strength". The term "Bloom" as used herein is defined as the weight in grams required to impress a one-half inch diameter plunger 4 mm into a gelatin solution containing 6 percent solids gelled at 10° C. for 17 hours. A suitable test procedure for determining bloom is outlined in *Industrial Engineering Chemistry*, Analytical Edition, vol. II, page 348, and vol. XVII, page 64. The maximum Bloom for gelatin is around 300. Three hundred (300) bloom gelatin is commercially available. Also available is "0 bloom" gelatin, which is also known as "hydrolyzed" gelatin. The term "non-hydrolyzed" is herein defined as a gelatin having a bloom number between 30 and 300. Gelatins having the Bloom values between 0 and 300 are also commercially available, e.g. 80, 100 and 270 bloom gelatin is currently offered by several manufacturers. Furthermore, the source and the preparation of the gelatin can vary. Sources include gelatin derived from the bone or skin from bovine or swine and the treatment of the gelatin source can be acid or alkaline followed by boiling in water. Those produced via acid treatment are referred to as Type A and those via alkaline as Type B. More recently gelatin derived from fish has become commercially available. The source and treatment can result in different properties, molecular weight, Bloom strength, as well as it ability to stabilize emulsions.

FLODEX Flowability

The term "flowability" as used herein refers to how free flowing a powder is. Specifically, free-flowing powders have a FLODEX® flowability of 50 or more. The FLODEX® flowability test is described in detail in U.S. Pat. No. 5,000,888, column 7, lines 55–70, column 8, lines 1–45, incorporated by reference herein.

Flowability can be measured with the FLODEX® method (Dow-Lepetit). A sample is placed in a smooth cylinder with a circular hole in the bottom. The whole is closed during filling. Once the complete amount of powder is filled in, the bottom hole is opened. A powder with a good flowability will flow through a small hole, whereas a powder with a poor flowability requires a large hole to leave the cylinder. The FLODEX® value is the reciprocal of the diameter in millimeters times 1,000 of the smallest hole through which the sample will pass. The maximum flowability is obtained in this test utilizing a flow disc having a four millimeter diameter orifice. In this case, the flow obtained is reported as equal to a value of 250. One skilled in the art understands that the value of 250 could imply a higher flowability because the standard flow disc orifice will only measure up to 250.

Malvern Measurement of Droplet Size

The oil-droplet size in the powder is measured with a Malvern Mastersizer S® which works on the principle of laser light diffraction. For the measurements, the 300RF lens with an active beam of 2.4 mm is used. The refractive indices used are (1.49, 0.00) for the vitamin E oil and (1.33, 0.00) for the dispersant water. A vitamin E powder or emulsion, about 0.2 g are dispersed in about 20 ml of hot water (50 to 60° C.). This dispersion is pipetted slowly in the water of the Small Volume Dispersion Unit (MS1), until the obscuration reaches the desired value of 10 to 30%. The stirrer of the Dispersion Unit is at about 50%. The measurement is evaluated using the Polydisperse Model with a no Channels killed setting on the Malvern Mastersizer®. The oil-droplet size distribution of vitamin E powders exhibits typically two peaks. The first peak has about the same oil-droplet size distribution as the corresponding emulsion. The second peak, the magnitude of which is typically smaller than that of the first peak, is an artifact due to silica used during the spray-drying process. For the oil-droplet size evaluation, we disregard the second peak. The measured oil-droplet size is the D[4,3] (volume averaged diameter) of the first peak. The measurement is always made in duplicate. While the separation of the first and second peak is usually easy for Type A pork skin and Croda SPA® gelatins, for other gelatins the two peaks can be overlapping. In these cases, the two peaks are separated by the minimum or the inflection point (if there is no minimum between the two peaks). If the separation between the peaks is not obvious, we define the first peak as ending at $2\mu$.

$\mu$ $\mu$ as used herein means micron.

SUMMARY

The present invention relates to a method of making a spray-dried powder containing edible oil-droplets suitable for tabletting comprising:
(a) 40 to 90% edible oil,
(b) 10 to 60% gelatin
comprising the steps of:
(a) dissolving said gelatin or a mixture of said gelatins in hot water;
(b) adding said edible oil to the gelatin in hot water to form an emulsion;
(c) homogenizing said emulsion formed in step (b) until the average oil-droplet size is $\leq 0.8$;
(d) Spray drying the homogenized emulsion from step (c). wherein further, said edible oil-droplets have an average diameter of $\leq 0.8\mu$.

All percentages are weight percent unless otherwise Indicated. Further, the percentage of edible oil is expressed as dry weight percent.

DETAILED DESCRIPTION

The present invention relates to a method of making a spray-dried powder containing edible oil-droplets suitable for tabletting comprising:
(a) 40 to 90% edible oil,
(b) 10 to 60% gelatin
comprising the steps of:
(a) dissolving said gelatin or a mixture of said gelatins in hot water;
(b) adding said edible oil to the gelatin in hot water to form an emulsion;
(c) homogenizing said emulsion formed in step (b) until the average oil-droplet size is $\leq 0.8$;
(d) Spray drying the homogenized emulsion from step (c). wherein further, said edible oil-droplets have an average diameter of $\leq 0.8\mu$.

All percentages are weight percent unless otherwise Indicated. Further, the percentage of edible oil is expressed as dry weight percent.

The oil-droplets in the powder or emulsion have an average diameter of less than or equal to $0.8\mu$, preferably less than or equal to $0.35\mu$.

PREPARING THE PRESENT INVENTION

The present invention is prepared by blending the edible oil and the gelatin to form a crude emulsion. Said emulsion is then subjected to high pressure homogenization to achieve the $\leq 0.8\mu$ edible oil-droplet size.

The preferred oil-droplet size is 0.05 to $0.8\mu$, more preferably 0.1 to $0.4\mu$, most preferably 0.25 to $0.35\mu$.

At oil loadings larger than 70%, the oil droplet should have an average diameter of less than $0.6\mu$, and preferably less than $0.45\mu$.

At oil loadings less than 55%, the oil droplet should have an average diameter less than $0.45\mu$, and preferably less than $0.35\mu$, and most preferably less than $0.30\mu$. While the high-pressure homogenizer is best suited for achieving small oil-droplets on a pilot or plant scale, other types of homogenizers can be used as well. Specifically, a shear-blade agitator results in an emulsion which can be spray dried to a powder having an oil-droplet size of $\leq 0.8\ \mu$.

Edible Fats and Oils Useful in the Practice of the Present Invention

Fats and oils useful in the practice of the present invention include, but are not limited to, flavoring and fragrance oils, vegetable oils, animal fats, and natural and synthetic fat-soluble vitamins selected from A,D,E and K or mixtures thereof. Preferably, the oils are vitamin oils. The most preferred vitamin oils are E and A. Said vitamin oils can be diluted with an inactive oil such as cotton seed, corn or peanut.

For example, vitamin A palmitate is generally sold in powder form as a 500 international units (iu)/gram powder. Vitamin A palmitate in its pure form has a potency of $1.817\times 106$ iu/gram. To make a 500 iu/gram powder with a total oil loading of 65% one would use 35% gelatin, 27.5% Vitamin A palmitate, and 37.5% of some inactive oil such as a cottonseed oil or some other similar triglyceride.

To make a vitamin E powder of 800 iu/gram or 80%, one would use 80% vitamin E oil and 20% gelatin. Because the market place may still require a 500 iu/gram (50%) vitamin E powder, this can also be achieved while taking advantage of the ease of processing of the present invention. A powder could be made containing 50% vitamin E oil, 15% vegetable oil, e.g. cottonseed oil, and 35% non-hydrolyzed gelatin. This product could spray drying using no special conditions and with faster drying times than powders at lower total oil loadings. Additionally, the various vegetable oils are seven to ten times less expensive than gelatin. A Vitamin E powder consisting of 50% vitamin E oil and 50% non-hydrolyzed gelatin can be mace if the oil droplet size is reduced to less than $0.30\mu$.

Said edible oils are present at levels of 40 to 90%, more preferably 50 to 80%, and most preferably 65 to 80%.

Gelatins Useful in The Practice of the Present Invention

Gelatins useful in the practice of the present invention include, but are not limited to Croda SPA® (45-85 Bloom), derived from specially tanned cow hides, or Type A or Type B derived from bovine skin, bovine bone, pork skin, fish. Said gelatins are present at levels of 10 to 60%, more preferably 20 to 50%, most preferably 20 to 35%.

Non-Hydrolyzed gelatins of all species are preferred.

Solids Useful in the Practice of the Present Invention

Solids may be optionally added. They may be dissolved or suspended in an oil such as cotton seed oil, corn oil, or fractionated triglycerides. For example, beta-carotene and other carotenoids, such as astaxanthin, canthaxantin, beta-apo-8-carotenal, are acceptable solids. The carotenoids are commonly used as suspensions in oil.

Furthermore, the solids may be suspended or dissolved in the aqueous phase during processing.

Further, some drug active substances are useful solids. Representative solid pharmaceuticals include, but are not limited to: antiinfectives such as antibiotics, and antiviral agents, analgesics, anorexics, antihelminthics, anti arthritics, antiasthmatics, anticonvulsants, antidepressants, antidiabetic agents, antidiarrheals, antihistamines, antiinflammatory agents, antimigraine preparations, anti nauseants, antineoplastics, antiparkinsonism drugs, antipruritics, antipsychotics, antipyretics, antispasmodics, anticholinergics, sympathomimetics, xanthine derivatives, cardiovascular preparations including calcium channel blockers, and beta blockers, and anti arrythmics, antihypertensives, diuretics, vasodilators including general coronary, peripheral and cerebral, central nervous system stimulants, cough and cold preparations including decongestants, hormones such as estradiol, and other steroids, including corticosteroids, hypnotics, immunosupressives, muscle relaxants, para sympatholytics, psychostimulants, sedatives and tranquilizers. Said pharmaceuticals are suspendible in the oil.

The levels of use of solids is typically 5 to 40% in the oils.

Excipients Useful in the Practice of the Present Invention

The term excipient is a catch-all term for diluents or vehicles for a drug. Excipients include: diluents or fillers, binders or adhesives, disintegrants, lubricants, antiadherents, glidants or flow promoters, colors, flavors, sweeteners and adsorbents Specifically, tablet fillers are substances that compromise the bulk of the tablet and primarily act as a carrier. Typical tablet fillers include, but are not limited to, calcium sulfate, calcium phosphate, calcium carbonate, starch, modified starches (carboxymethyl starch, etc.), microcrystalline cellulose, lactose, sucrose, dextrose mannitol and sorbitol.

Tablet filler levels are from about 10–90% by weight of the tablet.

Binders act as the "glue" which holds powders together to form granules. Binders include, but are not limited to, natural polymers such as starches or gums acacia, tragacanth and gelatin or synthetic polymers such as PVP and methyl-, ethyl- and hydroxypropylcellulose.

Binder levels are from about 1 to 10% of the formulation.

Disintegrants cause compressed tablets to break apart. Typical examples include, but are not limited to, starch, microcrystalline cellulose, purified wool starch, alginic acid, sodium starch glycolate guar gum, crosslinked polyvinyl pyrolidone (PVP), ion exchange resin and celluloses such as methyl-, sodium carboxymethyl- and hydroxypropylmethyl-.

Disintegrant levels are from about 0.5–15% of the formulation.

Lubricants reduce friction between the granulation and die wall during compression and ejection. Most lubricants are water insoluble and include stearates (magnesium, calcium and sodium), stearic acid, talc and waxes. Water soluble lubricants include PEG's, sodium benzoate, sodium oleate, sodium acetate, sodium lauryl sulfate and magnesium lauryl sulfate.

Lubricant levels are from about 0.25–5% of the formulation.

Antiadherents prevent sticking to the punch and to the die wall. Typical antiadherents include, but are not limited to, talc, cornstarch, silicon dioxide, sodium lauryl sulfate and metallic stearates.

Antiadherents levels are from about 0.1–5%. of the formulation.

Glidants improve the flow characteristics of the granulation. Typical glidants include, but are not limited to, talc cornstarch and silicas.

Glidant levels are from about 0.1–5% of the formulation.

Colorants are added to help identify types of tablets and for aesthetic purposes. Typical examples include colors designated as D&C and FD&C dyes and lakes.

Colorant levels are from about <1% of the formulation.

Flavors and sweeteners are commonly used to improve the taste of chewable tablets. Typical examples include, but are not limited to, natural sugars, aspartame (nondrug approved) and saccharin. Typical usage level is 25–50% for natural sugars and of formulation. Typical usage levels for aspartame and saccharin is >1%.

Adsorbents are typically silicon dioxides (Syloid, Cab-O-Sil, Aerosil). They retain large quantities are liquids without becoming wet.

Absorbent levels are from about 1 to 10% of the formulation.

See, Handbook of Pharmaceutical Excipients (Academy of Pharmaceutical Science of the American Pharmaceutical Association) and Pharmaceutical Dosage Forms: Tablets edited by Lieberman, Lachman and Schwartz for a detailed description of excipients useful in the practice of the present invention.

The following non-limiting Examples 1–19, illustrate how to prepare the high oil loading vitamin E powder suitable for tabletting of the present invention.

Example 20 illustrates how to prepare a vitamin A derivative, (13-cis-Retinoic acid powder) taking advantage of the ease of processing of the present invention.

EXAMPLE 1
Vitamin E-650 With Large Oil-Droplets 1701 g of non-hydrolyzed Croda SPA® gelatin is dissolved in 6876 g hot water (60° C.) using a Gifford-Wood® Rotor-Stator Homogenizer (Model 2L). 3425 g of vitamin E oil (food grade) is added to the solution and emulsified for 10 minutes with the Gifford-Wood ® homogenizer. The average oil-droplet size in the emulsion is about 3 $\mu$ as measured by the Malvern Mastersizer®. The emulsion is spray dried in a Niro® Utility Spray Drier with centrifugal atomization (wheel speed 12,000 RPM, feed temperature 80° C., air inlet temperature 160° C., air outlet temperature 100° C., feed flow rate 190 g/min). Syloid 74®, silicon dioxide, is added to the spraying chamber as flow aid (1 g/min) metered with K-tron® screw feeder.

EXAMPLE 2
Vitamin E-650 With Small Oil-Droplets

The emulsion is prepared as in Example 1, but before spray drying it is passed once through a Niro-Soavi® high-pressure homogenizer (Model 2006) at 1,000 bar pressure drop. The homogenization step results in an average oil-droplet size of 0.43 $\mu$ in the emulsion. The emulsion is spray dried as in Example 1.

EXAMPLE 3
Vitamin E-650 With Very Small Oil-Droplets

The emulsion is prepared as in Example 2 (6626 g water, 1784 g gelatin, and 3590 g vitamin E oil), however, it is passed 4 times through the Niro-Soavi® high-pressure homogenizer (1,000 bar). The homogenization results in an average oil-droplet size of 0.29$\mu$ in the emulsion. The emulsion is spray dried as in Example 1.

EXAMPLE 4
Vitamin E-700 With Very Small Oil-Droplets

The emulsion is prepared as in Example 1 but with higher oil loading (6912 g water, 3853 g vitamin E oil, 1482 g Croda SPA® gelatin). The emulsion is passed three times through the Niro-Soavi® high-pressure homogenizer resulting in an emulsion oil-droplet size of 0.28$\mu$. The emulsion is spray dried as in Example 1.

EXAMPLE 5
Vitamin E-600 With Very Small Oil-Droplets

The emulsion is prepared, homogenized and spray dried as in Example 4 but with lower oil loading (6966 g water, 1951 g Croda SPA® gelatin, 3083 g vitamin E oil). The average oil-droplet diameter in the emulsion before spray drying is 0.25$\mu$.

EXAMPLE 6
Vitamin E-550 With Very Small Oil Droplets

The emulsion is prepared, homogenized and spray dried as in Example 5 but with lower oil loading (7185 g water, 2125 g Croda SPA® gelatin, 2693 g vitamin E oil). The average oil-droplet diameter in the emulsion before spray drying is 0.26$\mu$.

EXAMPLE 7
Vitamin E-500 With Very Small Oil-Droplets

The emulsion was prepared, homogenized and spray dried as in Example 6 but with lower oil loading (7159 g water, 2338 g Croda SPA® gelatin, 2503 g vitamin E oil). The average oil-droplet diameter in the emulsion before spray drying was 0.26 $\mu$. Since only little product is collected at 12,000 RPM (indicating that the limit of sprayability of non-hydrolyzed Croda SPA® gelatin had been reached), the wheel speed was increased to 19,000 RPM.

EXAMPLE 8
Vitamin E-750 With Very Small Oil-Droplets

The emulsion was prepared as in Example 4 but with higher oil loading (6575 g water, 4215 g vitamin E oil, 1209 g Croda SPA® gelatin). The emulsion was passed three times through the Niro-Soavi® high-pressure homogenizer resulting in an emulsion oil-droplet size of 0.28$\mu$. The emulsion was spray dried as in Example 1.

EXAMPLE 9
E-650 With Non-Hydrolyzed Type A Pork Skin Gelatin (100 Bloom)

The emulsion was prepared, homogenized and spray dried as in Example 4 but with a different recipe (6501 g water, 1825 g type A pork skin low bloom gelatin, 3674 g vitamin E oil). The average oil droplet diameter in the emulsion before spray drying was 0.32$\mu$.

EXAMPLE 10
E-650 With Non-Hydrolyzed Type A Pork Skin Gelatin (250 Bloom)

The emulsion was prepared, homogenized and spray dried as in Example 4 but with a different recipe (8251 g water, 1245 g type A pork skin high bloom gelatin, 2505 g vitamin E oil). The average oil-droplet diameter in the emulsion before spray drying was 0.32 $\mu$.

EXAMPLE 11
E650 With Non-Hydrolyzed Type B Bone Gelatin (250 Booom)

The emulsion was prepared, homogenized and spray dried as in Example 4 but with a different recipe (7376 g water, 1369 g type B bone high bloom gelatin, 2759 g vitamin E oil) and 5 passes through the high-pressure homogenizer. The average oil-droplet diameter in the emulsion before spray drying was 0.31$\mu$.

EXAMPLE 12
E650 With Non-Hydrolyzed Type B Calf Skin Gelatin (220 Bloom)

The emulsion was prepared, homogenized and spray dried as in Example 4 but with a different recipe (7876 g water, 1535 g type B calf skin high bloom gelatin, 3091 g vitamin E oil). The average oil-droplet diameter in the emulsion before spray drying was 0.43$\mu$.

EXAMPLE 13
E-650 With Hydrolyzed Croda SPA® Gelatin

The emulsion was prepared, homogenized and spray dried as in Example 4 but with a different recipe (5660 g water, 1710 g Croda SPA® gelatin, 3445 g vitamin E oil, 7 g Sodium Benzoate, 4 g Potassium Sorbate, 3 g HT Proteolytic 200 in water). After hydrolysis the MW of the gelatin was 15,400. The average oil-droplet diameter in the emulsion before spray drying was 0.32$\mu$.

EXAMPLE 14
E650 With Non-Hydrolyzed Fish Gelatin (250 Bloom)

The emulsion was prepared, homogenized and spray dried as in Example 4 but with a different recipe (7251 g water, 1576 g fish gelatin, 3173 g vitamin E oil) and 19,000 RPM homogenizer wheel speed. The average oil droplet diameter in the emulsion before spray drying was 0.33$\mu$.

EXAMPLE 15
E-700 With Non-Hydrolyzed Type A Pork Skin Gelatin (250 Bloom)

The emulsion was prepared, homogenized and spray dried as in Example 4 but with a different recipe (7283 g water, 1310 g type A pork skin high bloom gelatin, 3407 g vitamin E oil). The average oil droplet diameter in the emulsion before spray drying was 0.29$\mu$.

EXAMPLE 16
E-700 With Non-Hydrolyzed Type A Pork Skin Gelatin (275 Bloom)

The emulsion was prepared, homogenized and spray dried as in Example 4 but with a different recipe (7779 g water, 1172 g type A pork skin high bloom gelatin, 3050 g vitamin E oil). The average oil droplet diameter in the emulsion before spray drying was 0.30$\mu$.

EXAMPLE 17
E-700 With Non-Hydrolyzed Type A Bone Gelatin (280 Bloom)

The emulsion was prepared, homogenized and spray dried as in Example 4 but with a different recipe (8283 g water, 1310 g type A pork skin high bloom gelatin, 3407 g vitamin E oil). The average oil-droplet diameter in the emulsion before spray drying was 0.29$\mu$.

EXAMPLE 18
E-750 With Non-Hydrolyzed Type A Pork Skin Gelatin (250 Bloom)

The Emulsion is prepared, homogenized and spray dried as in Example 4 but with a different recipe (7808 g water, 934 g type A pork skin high bloom gelatin, 3258 g vitamin E oil). The average oil droplet diameter in the emulsion before spray drying is 0.30$\mu$. The resulting powder is analyzed for oil droplet size (0.52$\mu$), tablet hardness (10 SCU), flowability (Flodex =84), and tapped density (=0.45 g/cm3).

EXAMPLE 19
E-800 With Non-Hydrolyzed Type A Pork Skin Gelatin (250 Bloom)

The Emulsion is prepared, homogenized and spray dried as in Example 4 but with a different recipe (7715 g water, 787 g type A pork skin high bloom gelatin, 3500 g vitamin E oil), and a different flow aid, Aerosil 200. The potency of the vitamin E oil is 99.3%. The average oil droplet diameter in the emulsion before spray drying is 0.40 $\mu$. The resulting powder is analyzed for oil droplet size (0.50$\mu$), tablet hardness (5 SCU), flowability (Flodex =56), and tapped density (=0.44 g/cm3).

EXAMPLE 20
13-Cis Retinoic Acid in Oil Suspension With Croda Spa® Gelatin 1482 g of non-hydrolyzed Croda® SPA gelatin is dissolved in 6912 g hot water (60° C.) using a Gifford-Woods® Rotor-Stator Homogenizer (Model 2L). 3853 g of 30% 13-cis-retinoic acid micronized in vegetable oil is added to the solution and emulsified for 10 minutes with the Gifford-Woods® homogenizer. The emulsion is passed three times through the Niro-Soavi® high-pressure homogenizer. The emulsion is spray dried as in Example 1.

The spray dried emulsions prepared as described in Examples 1–19, were then evaluated for tabletting. Specifically, the stringent tabletting formulation in TABLE 1 (in that it relies entirely on the vitamin E powder for binding the tablet together) was used for evaluating the spray-dried formulations of Examples 1–19.

TABLE 1

| | GRAMS/TABLET | |
|---|---|---|
| | Ingredient | g/tablet |
| 1 | Vitamin E Powder 500 to 800 iu/g | 0.4000 |
| 2 | Syloid ™ 244FP | 0.0150 |
| 3 | Cab-O-Sil ™ HS-5 | 0.0100 |
| 4 | Microcel C (calcium silicate) | 0.0082 |

This tabletting formulation is very good at giving an indication of how well the vitamin E oil is encapsulated. If the oil is not encapsulated, tablets are prone to be spotted and the tablets will be soft. Softness is also dependent on the compressibility of the excipients. These tablets were made on an instrumented Manesty B3B Press® with 7/16 standard concave punches at a pressure of 8,000 lbs. The tablets were tested for hardness on a Schleuniger® Model 2E or 4E hardness testers. The hardness values are given in Strong-Cobb Units (SCU). The maximum hardness that can be measured is 64 SCU. Generally, the harder the tablets are the better they are. In this formulation a tablet hardness around 10 SCU was considered minimally acceptable.

TABLE 2 illustrates the properties of spray dried high oil loading powders compressed into tablets from the powder formed in Examples 1–19.

TABLE 3-continued

Detailed Comparison of High-Potency Vitamin E powders

| Characteristic | Example 18 (present invention) | Roche E-75 (current technology) | Example 19 (present invention |
|---|---|---|---|
| During Tableting | No Problems | separating from rest of mix Tablets sticking to punches. Pieces of tablets left on tablets. Build up of oily shavings | Some powder sticking to upper and lower punches |

TABLE 2

PROPERTIES OF SPRAY-DRIED POWDERS FROM EXAMPLES 1 TO 19

| EXAMPLE | 1 | 2 | 3 | 4 | 5 | 6 | 7 | 8 | 9 | 10 |
|---|---|---|---|---|---|---|---|---|---|---|
| Active Oil Loading (%) | 65 | 65 | 65 | 70 | 60 | 55 | 50 | 75 | 65 | 65 |
| Actual Vitamin E-acetate (97%) | 67.7 | 67.7 | 67.7 | 72.7 | 62.5 | 57.4 | 53.4 | 77.7 | 67.7 | 67.7 |
| Oil-droplet size-d[4,3](m) | 2 | 0.45 | 0.29 | 0.33 | 0.27 | 0.27 | 0.27 | 0.3 | 0.37 | 0.35 |
| Tablet Hardness (SCU) | 2 | 13 | 40 | 16 | 62 | >64 | >64 | 6 | 28 | 28 |
| Flodex Flowability | 38 | 71 | 83 | 100 | 83 | 63 | 38 | 100 | 100 | 56 |
| Tapped Density (g/cm3) | 0.42 | 0.48 | 0.53 | 0.54 | 0.52 | 0.55 | 0.49 | 0.45 | 0.52 | 0.46 |
| Gelatin (%) | 29.6 | 29.6 | 29.6 | 24.6 | 34.8 | 39.9 | 43.9 | 19.6 | 29.6 | 29.6 |
| Moisture (%) | 2 | 2 | 2 | 2 | 2 | 2 | 2 | 2 | 2 | 2 |
| Silicon dioxide (%) | 0.7 | 0.7 | 0.7 | 0.7 | 0.7 | 0.7 | 0.7 | 0.7 | 0.7 | 0.7 |
| Actual Potency *IU/g) | 657 | 657 | 657 | 705 | 606 | 557 | 518 | 754 | 657 | 657 |

| EXAMPLE | 11 | 12 | 13 | 14 | 15 | 16 | 17 | 18 | 19 |
|---|---|---|---|---|---|---|---|---|---|
| Active Oil Loading (%) | 65 | 65 | 65 | 65 | 70 | 70 | 70 | 75 | 80 |
| Actual Vitamin E-acetate (97%) | 67.7 | 67.7 | 67.7 | 67.7 | 72.7 | 72.7 | 72.7 | 77.7 | 80.5† |
| Oil-droplet size-d[4,3](m) | 0.34 | 0.37 | 0.36 | 0.36 | 0.32 | 0.45 | 0.35 | 0.52 | 0.5 |
| Tablet Hardness (SCU) | 23 | 28 | 15 | 31 | 31 | 24 | 22 | 10 | 5 |
| Flodex Flowability | 71 | 56 | 100 | 50 | 71 | 200 | 100 | 84 | 56 |
| Tapped Density (g/cm3) | 0.46 | 0.51 | 0.53 | 0.47 | 0.47 | 0.48 | 0.51 | 0.45 | 0.44 |
| Gelatin (%) | 29.6 | 29.6 | 29.6 | 29.6 | 24.6 | 24.6 | 24.6 | 19.6 | 16.1 |
| Moisture(%) | 2 | 2 | 2 | 2 | 2 | 2 | 2 | 2 | 1.4 |
| Silicon dioxide (%) | 0.7 | 0.7 | 0.7 | 0.7 | 0.7 | 0.7 | 0.7 | 0.7 | 2 |
| Actual Potency *IU/g) | 657 | 657 | 657 | 657 | 705 | 705 | 705 | 754 | 800† |

†The actual potency of the vitamin E oil used in this example is 99.3%

Utility of the Present Invention In Tabletting

Once the emulsion is spray dried to a powder as described in Examples 1–19, it can be tabletted according to methods known to those skilled in the art. See, *Pharmaceutical Dosage Forms, Tablets,* 2nd. Ed. 1989, Vols 1, 2, 3, Editors H. A. Lieberman, L. Lachman, J. B. Schwartz.

TABLE 3 hereinbelow illustrates the superior benefits of the present invention over the current technology.

TABLE 3

Detailed Comparison of High-Potency Vitamin E powders

| Characteristic | Example 18 (present invention) | Roche E-75 (current technology) | Example 19 (present invention |
|---|---|---|---|
| Vitamin E Powder Potency (iu/gm) | 750 | 750 | 800 |
| Ingredient Mixing | No Problems | Mixing of the formulation difficult. Cab-O-Sil | No Problems |

TABLE 3-continued

Detailed Comparison of High-Potency Vitamin E powders

| Characteristic | Example 18 (present invention) | Roche E-75 (current technology) | Example 19 (present invention |
|---|---|---|---|
| Average Compression Force used (lbs) | 8073 | around the top punches 8195 | 8267 |
| Compression Force Coefficient of Variation-CV (%) | 2.8 | 8.7 | 3.0 |
| Tablet Appearance | Slightly oily on surface but typical. Tablets uniform with no pieces missing. | Tablets oily on surface. Oily wet spots indicate the vitamin E has pressed out. Tablets not uniform with pieces missing | Slightly oily on surface but typical Tablets uniform with no pieces missing. |

TABLE 3-continued

Detailed Comparison of High-Potency Vitamin E powders

| Characteristic | Example 18 (present invention) | Roche E-75 (current technology) | Example 19 (present invention |
|---|---|---|---|
| Tablet weight CV (%) | 1.2 | 29.8 | 0.7 |
| Tablet Hardness (SCU) | 10.3 | 1.4 (tablets crumbled into powder) | 5.3 |
| Tablet Hardness CV (%) | 8.0 | 0.89 | 6.3 |

The coefficient of variation (CV) is the standard deviation divided by the average multiplied by 100.

The results in Table 3 are the average of 10 samples, i.e. 10 tablets were made from the spray dried emulsion prepared in Examples 18 and 19.

We claim:

1. A method for making a spray-dried powder containing edible oil droplets comprising:
   (a) 40 to 90% edible oil,
   (b) 10 to 60% gelatin wherein further, said edible oil droplets have an average diameter of $\leq 0.8\mu$.

comprising the steps of:
   (a) dissolving said gelatin or a mixture of a said gelatins in hot water;
   (b) adding said edible oil to the gelatin in hot water to form an emulsion;
   (c) homogenizing said emulsion formed in step (b) until the average oil-droplet size is $\leq 0.8\ \mu m$,
   (d) Spray drying the homogenized emulsion from step (c).

2. A method according to claim 1, wherein said edible oil is vitamin E.

3. A method according to claim 1, wherein said gelatin is unhydrolyzed.

4. A method according to claim 1, wherein said edible oil content is 50–80%.

5. A method according to claim 1, wherein said gelatin content is 20–50%.

6. A method according to claim 1, wherein said edible oil content is 65–80%.

7. A method according to claim 1, wherein said gelatin content is 20–35%.

* * * * *